(12) United States Patent
da Conceição Moutinho et al.

(10) Patent No.: US 12,064,642 B2
(45) Date of Patent: *Aug. 20, 2024

(54) SYSTEM AND METHOD FOR ADAPTIVE RADIOTHERAPY

(71) Applicant: NU-RISE Lda, Ilhavo (PT)

(72) Inventors: Luis Miguel da Conceição Moutinho, Aveiro (PT); Joana Isabel Ferreira dos Santos Melo, Aveiro (PT)

(73) Assignee: NU-RISE Lda (PT)

( * ) Notice: Subject to any disclaimer, the term of this patent is extended or adjusted under 35 U.S.C. 154(b) by 145 days.

This patent is subject to a terminal disclaimer.

(21) Appl. No.: 17/832,780

(22) Filed: Jun. 6, 2022

(65) Prior Publication Data

US 2022/0305286 A1 Sep. 29, 2022

Related U.S. Application Data

(63) Continuation of application No. 16/713,577, filed on Dec. 13, 2019, now Pat. No. 11,383,100.

(51) Int. Cl.
*A61N 5/10* (2006.01)
*A61N 5/01* (2006.01)

(52) U.S. Cl.
CPC ............. *A61N 5/1007* (2013.01); *A61N 5/01* (2013.01); *A61N 5/1027* (2013.01); *A61N 5/1071* (2013.01); *A61N 2005/1008* (2013.01)

(58) Field of Classification Search
CPC .......................................... A61N 5/1001–1029
See application file for complete search history.

(56) References Cited

U.S. PATENT DOCUMENTS

| 6,728,335 | B1 * | 4/2004 | Thomson ............. A61N 5/1001 378/92 |
| 2010/0288934 | A1 | 11/2010 | Keppel | |
| 2014/0051904 | A1 * | 2/2014 | Solf ..................... G01V 5/0041 600/3 |
| 2014/0350325 | A1 | 11/2014 | Van Appeldoorn et al. | |
| 2018/0085597 | A1 | 3/2018 | Isham | |

FOREIGN PATENT DOCUMENTS

| WO | 2013012331 A1 | 1/2013 |
| WO | 2016093942 A2 | 6/2016 |

OTHER PUBLICATIONS

Int'l Search Report and Written Opinion Appln No. PCT/US2020/001030 mailed May 3, 2021.

* cited by examiner

*Primary Examiner* — Thaddeus B Cox
(74) *Attorney, Agent, or Firm* — McAndrews, Held & Malloy, Ltd.

(57) ABSTRACT

Interstitial brachytherapy is a cancer treatment in which radioactive material is placed directly in the target tissue of the affected site using an afterloader. The accuracy of radiation placement is monitored during the cancer treatment. The location plan for the radioactive material may be adjusted during the cancer treatment based on real-time analysis of the location and dosage of radiation measured in, at and around the target tissue of the affected site.

20 Claims, 9 Drawing Sheets

SYSTEM AND METHOD FOR ADAPTIVE RADIOTHERAPY

The present application is a continuation of U.S. application Ser. No. 16/713,577, filed Dec. 13, 2019, now U.S. Pat. No. 11,383,100. The aforementioned documents are hereby incorporated herein by reference in their entirety.

BACKGROUND

Limitations and disadvantages of conventional approaches to data storage will become apparent to one of skill in the art, through comparison of such approaches with some aspects of the present method and system set forth in the remainder of this disclosure with reference to the drawings.

BRIEF SUMMARY

Methods and systems are provided for adaptive radiotherapy substantially as illustrated by and/or described in connection with at least one of the figures, as set forth more completely in the claims.

DETAILED DESCRIPTION

Brachytherapy is commonly used as an effective treatment for cervical, prostate, breast, esophageal and skin cancer, and can also be used to treat tumors in many other body sites. Interstitial brachytherapy is a cancer treatment in which a source of ionizing radiation is placed closely to the tumor target tissue of the affected site, such as the prostate or breast. The ionizing radiation can be delivered by a plurality of ways, namely an isotope with low activity (LDR-brachytherapy) up to high activity (HDR-brachytherapy) or by an X-ray emitter (electronic brachytherapy).

The dose rate of brachytherapy refers to the level or intensity with which the radiation is delivered to the surrounding medium and is expressed in Grays per hour (Gy/h). In high-dose rate (HDR) brachytherapy, the rate of dose delivery typically exceeds 12 Gy/h. During HDR brachytherapy, radiation sources are placed for a set duration (usually a number of minutes or hours) before being withdrawn. The specific treatment duration will depend on many different factors, including the required rate of dose delivery and the type, size and location of the cancer.

A range of imaging technologies (e.g., x-ray radiography, ultrasound, computed axial tomography (CT or CAT) scans and magnetic resonance imaging (MRI)) can be used to visualize the shape and size of the tumor and its relation to surrounding tissues and organs. The data from many of these sources can be used to create a 3D map of the tumor and the surrounding tissues. Using this information, a plan of the optimal distribution of the radiation sources can be developed. This includes consideration of how the radiation should be placed and positioned. Errors or poor treatment setup might present a safety risk to the patient. Too little irradiation or too much irradiation must be avoided during treatment, as these can result in treatment failure and severe side-effects.

Figure 1:
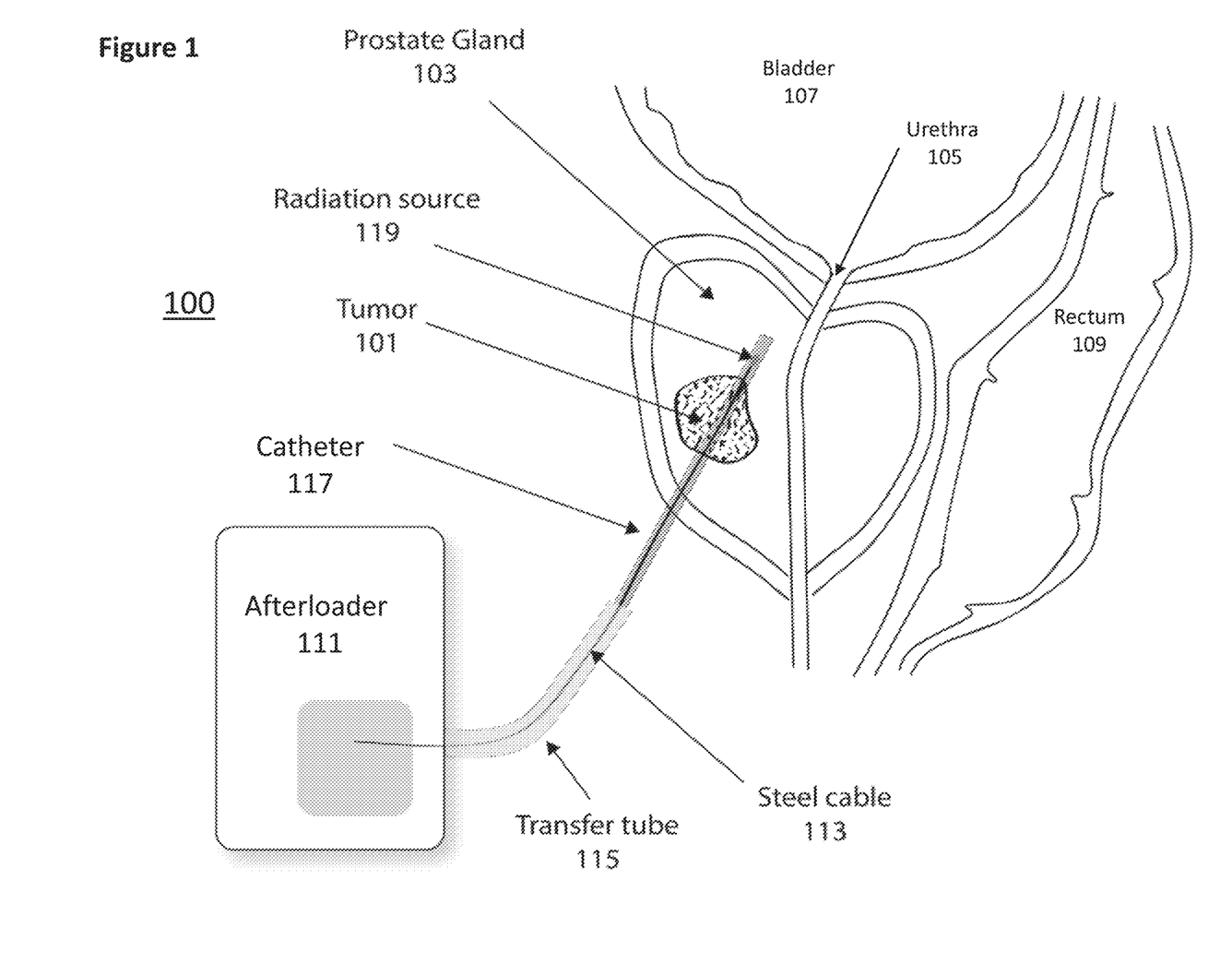
FIG. 1 illustrates an example interstitial brachytherapy treatment using an afterloader directed at a tumor in a patient's prostrate in accordance with aspects of this disclosure.

FIG. 1 illustrates an example interstitial brachytherapy treatment 100 of a tumor 101 in a patient's prostate gland 103 in accordance with aspects of this disclosure. The size and location of the tumor 101 relative to the patient's urethra 105, bladder 107 and rectum 109 as shown is for illustration purposes. The tumor 101 may be any size and located anywhere in the prostate 103.

As shown in FIG. 1, an afterloader 111 is a radiotherapy machine being used to radiate the tumor 101. The afterloader 111 has the ability to place an ionizing radiation source 119 into the patient treatment area. The ionizing radiation source may be an isotope fixed in the extremity of a steel cable 113 that the afterloader 111 controls and sends through transfer tube 115 into a plastic or metallic catheter 117 that is placed in the patient body. The ionizing radiation source may also be a miniaturized X-ray emitter at the end of a cable 114 that may be small enough to be placed into the a plastic or metallic catheter 117 through a transfer tube 115. Once located, the catheter 117 receives the radiation source 119, and the afterloader 111 controls the movement, positioning and dwell time of the radiation source 119 within the tumor 101 as specified by a doctor's treatment plan.

Interstitial brachytherapy requires the precise placement of short-range radiation sources 119 (e.g., radioisotopes Cobalt-60, Iodine-125, Cesium-131, Iridium-192, etc. or electronic sources such as miniaturized X-ray sources) directly at the site of a cancerous tumor 101. Radiation treatment is intended to kill cancerous tissue while reducing exposure to healthy tissues. The radiation source 119 may travel throughout the catheter 117 length, while stopping for pre-determined time periods in specific positions, thus providing irradiation of the surrounding tissues of the tumor 101 in an isotropic way. However, if the afterloader is not properly calibrated, healthy (e.g., non-cancerous) tissues may be irradiated in error.

Figure 2:
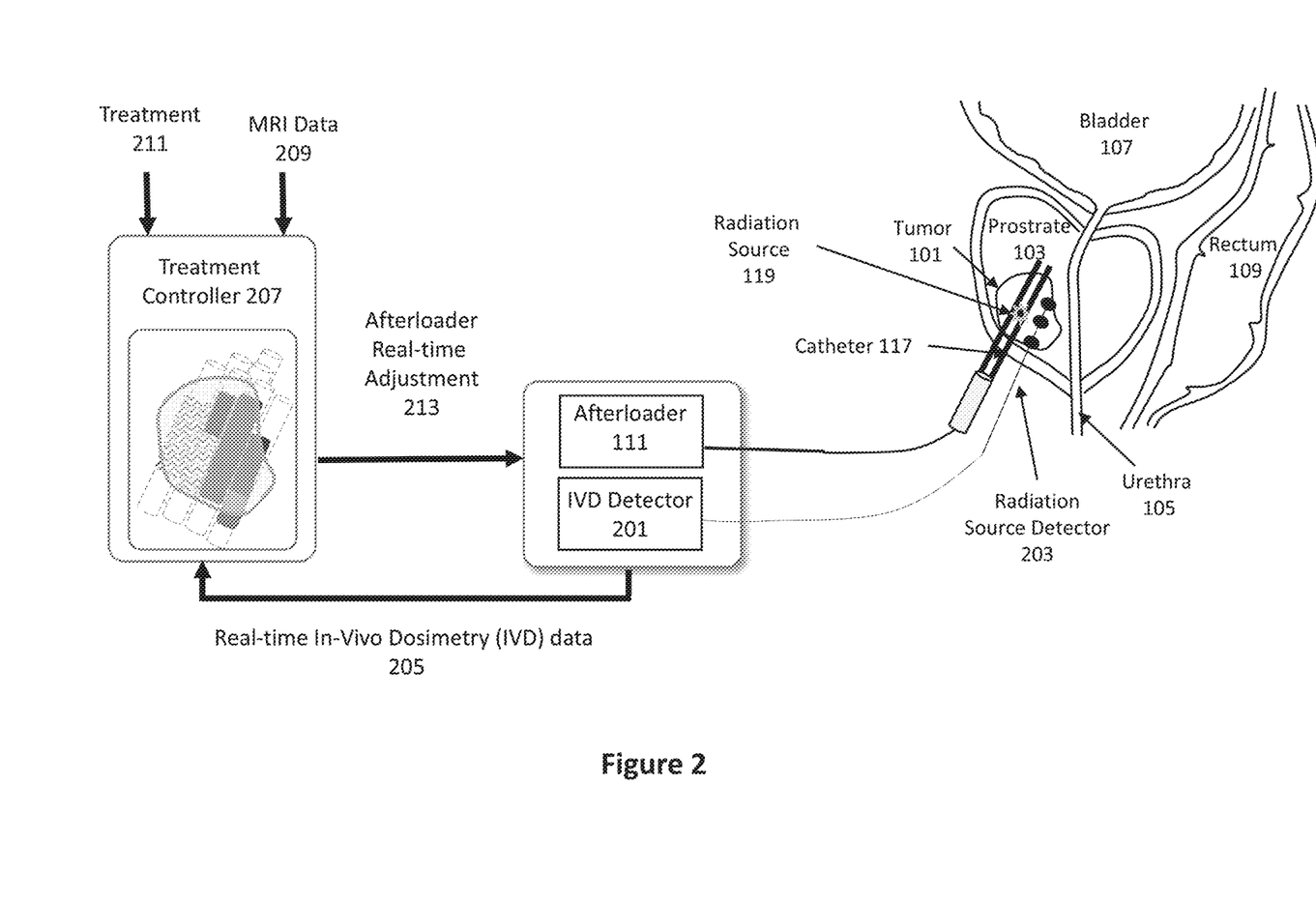
FIG. 2 illustrates an exemplary embodiment of a system for adaptive radiotherapy in accordance with aspects of this disclosure.

Aspects of the present disclosure provide a tool for adapting an afterloader radiotherapy machine in real-time, during the brachytherapy, to provide and maintain accurate radiation placement and dosage. The intensity, position and velocity of detected radiation can be used as feedback to recalibrate the afterloader in real-time. FIG. 2 illustrates an exemplary embodiment of a system for adaptive radiotherapy in accordance with aspects of this disclosure.

The treatment controller 207 can receive in-vivo dosimetry (IVD) data 205 and produce an afterloader adjustment signal 213. The treatment controller 207 can be embodied in a variety of forms. For example, the treatment controller 207 may be software on dedicated system or a mobile device such as an iPad or and iPhone. The treatment controller 207 may be programmed with a doctor's treatment plan 211 and MRI data 209. During radiotherapy, the IVD data 205 and the afterloader adjustment signal 213 may communicate wirelessly (or be directly wired) to an afterloader 111 and/or an IVD detector 201. The wireless communication may be accomplished via a variety of protocols such as WiFi, cellular, 5G or Bluetooth. A cellular connection, for example, would allow a doctor (or multiple doctors) to monitor the radiotherapy from a remote location. The treatment controller 207 may also be a feature that is added to the afterloader 111.

The IVD data 205 may be produced according to light received by a plurality of light detection units (e.g., photodetectors, photodiodes, etc. . . . ). The light detection units typically have a fast signal response time to allow for the identification of the radiation source position. The light detection units may be located in a radiation source detector 203 at the patient. Alternatively, the light detection units may be coupled to optical fibers and located in the IVD detector 201. The IVD detector 201 may be a stand-alone device or the IVD detector 201 may be added to the afterloader 111.

The light received by the plurality of light detection units is produced by a plurality of scintillators in the radiation source detector 203. Each scintillator of the plurality of scintillators is configured to produce light in a presence of ionizing radiation from the radiation source 119.

The location and velocity of the radiation source 119 may be calculated according to the electrical signals (e.g., voltage or current) from the plurality of light detection units. This calculation may be performed in the IVD detector 201 or the treatment controller 207.

The treatment controller 207 may map the progression of the radiotherapy and compare such a map to the MRI data 209 and the doctor's treatment plan 211 determined prior to radiotherapy. The treatment controller 207 may identify errors between a desired dosage of radiation and a current dosage of radiation according to the IVD data. Likewise, the treatment controller 207 may identify errors between a desired location of the radiation and a current location of the radiation. The afterloader adjustment signal 213 is determined according to the identified locations where the current treatment does not match the doctor's treatment plan 211.

Figure 3:
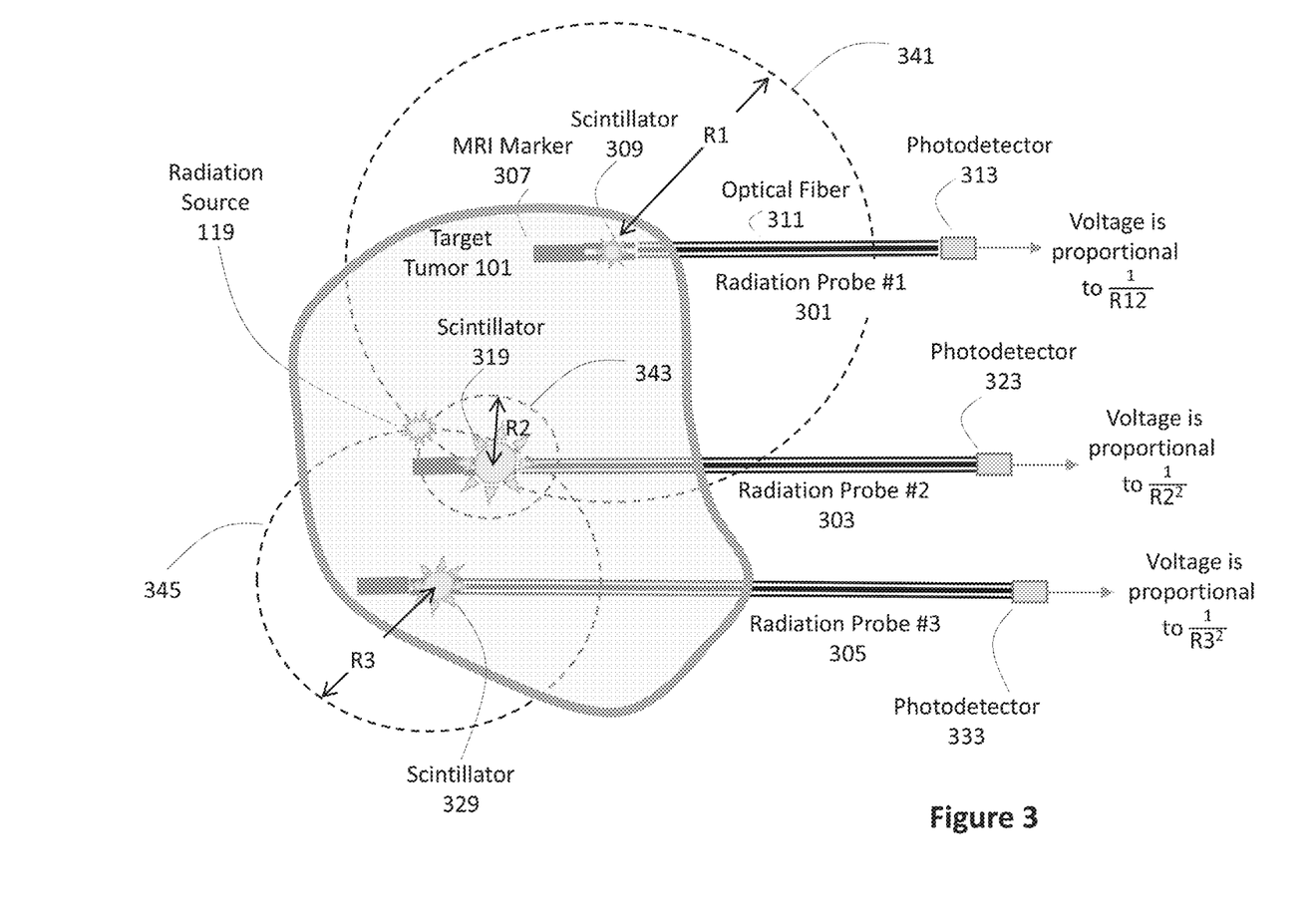
FIG. 3 illustrates an exemplary arrangement of radiation sensors in a system for adaptive radiotherapy in accordance with aspects of this disclosure.

According to an example embodiment, the radiation source detector 203 may comprise a plurality of radiation sensors/probes. FIG. 3 illustrates an exemplary arrangement of radiation sensors in a system for adaptive radiotherapy in accordance with aspects of this disclosure. The exemplary arrangement in FIG. 3 comprises radiation probe #1 301, radiation probe #2 303, and radiation probe #3 305.

Radiation probe #1 301 is illustrated with further detail. Radiation probe #1 301 comprises a scintillator 309 and may comprehend a photodetector 313 (e.g., photodiode). Additionally, radiation probe #1 301 may also comprise a fiducial marker 307 and/or an optical fiber 311. The fiducial marker 307 may comprise a gold tip that allows the radiation probe #1 301 to be located with an MRI scanner. The optical fiber 311 allows the photodetector 313 to be located at a distance from the scintillator 309. The photodetector 313 may also comprise a built-in lens and/or optical filter to select the wavelengths emitted from a particular scintillator 309.

When the radiation source 119 in tumor 101, radiation probe #1 301, radiation probe #2 303, and radiation probe #3 305 each produce an electrical signal that is inversely proportional to a function of the respective distances R1, R2, R3 between the radiation source 119 and the scintillator of each respective radiation probe 301, 303, 305. For example, an electrical signal thus produced may be inversely proportional to the square of the distance between radiation source 119 and the point 309 where radiation is converted to light. Each calculated distances R1, R2, R3 produces a sphere 341, 343, 345 of possible locations of radiation source 119. The intersection of the spheres 341, 343, 345 identify the radiation source 119 location. Thus, the electrical signals radiation probe #1 301, radiation probe #2 303, and radiation probe #3 305 are used to triangulate the position of a radiation source 119.

Each scintillator 309, 319, 329 is configured to produce light in a presence of radiation from a radioactive source of radiation 119. The level of the light produced by each scintillator 309, 319, 329 is proportional to the level of the radiation incident to each scintillator 309, 319, 329. Each light detection unit 313, 323, 333 is configured to produce an electrical signal in a presence of the light from one scintillator of the plurality of scintillators 309, 319, 329. The level of the electrical signal produced by each light detection unit 313, 323, 333 is proportional to the light incident to each light detection unit 313, 323, 333. Thus, the level of the electrical signal produced by each light detection unit 313, 323, 333 is proportional to the level and nature (e.g., spectral characteristics) of the radiation incident to each scintillator 309, 319, 329. Each light detection unit of the plurality of light detection units 313, 323, 333 may be coupled to one scintillator of the plurality of scintillators 309, 319, 329 via an optical fiber.

Figure 4:
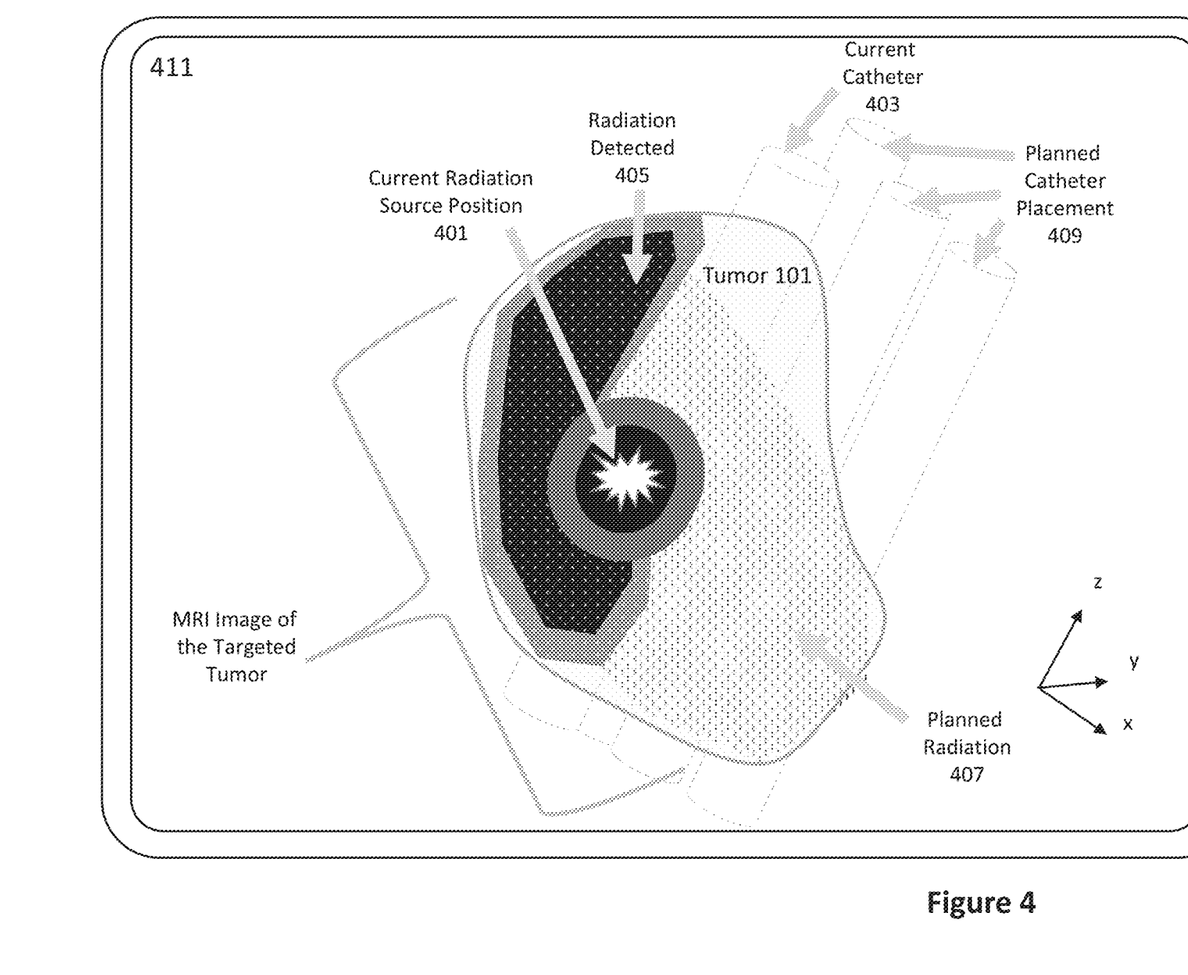
FIG. 4 illustrates an exemplary visual display on a treatment controller in a system for adaptive radiotherapy in accordance with aspects of this disclosure.

FIG. 4 illustrates an exemplary visual display 411 on a treatment controller 207 in a system for adaptive radiotherapy as shown in FIG. 2, for example. The visual display 411 is capable of mapping the radiation dosage. For example, the visual display 411 may be 3D and may use different colors and textures to identify a gradient of different radiation levels.

The visual display 411 is capable of combining an MRI image of a targeted tumor 101 with the doctor's treatment plan and the real-time feedback from the radiation monitoring. As illustrated, for example, the current position of the radiation source 401 may be overlaid on the MRI image of a targeted tumor 101. The doctor's treatment plan may be illustrated by an image of the current afterloader catheter placement 403 and the images of the planned afterloader catheter placement 405. Based on the radiation detected 405 and the planned radiation 407, the treatment controller 207 may compute whether a corrective measure should be made to the doctor's treatment plan. For example, the radiation may be targeting other regions than originally planned before the radiotherapy began. Such a corrective measure would be sent to change the current afterloader settings. Before the treatment controller changes the afterloader settings, a doctor may be given the option to override the treatment controller's adaptive response.

Figure 5:
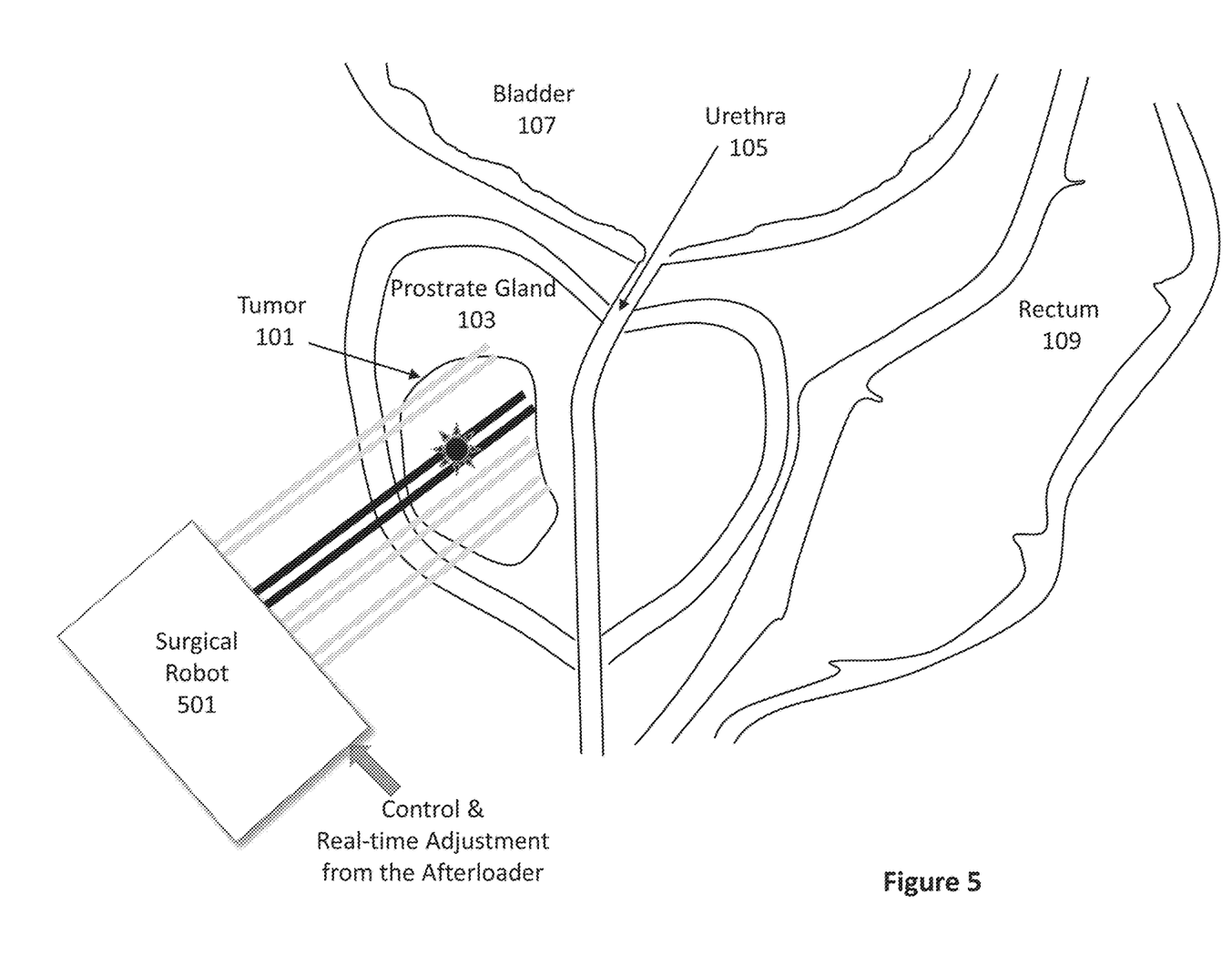
FIG. 5 illustrates the first placement option for an exemplary surgical robot in a system for adaptive radiotherapy in accordance with aspects of this disclosure.

FIG. 5 illustrates the first placement option for an exemplary surgical robot 501 in a system for adaptive radiotherapy in accordance with aspects of this disclosure. A surgical robot 501 may be configured to control the placement of one or more catheters according to the treatment controller adjustment instruction. For example, the surgical robot 501 may comprise a plurality of interstitial catheters that are directed to different locations within a patient.

Alternately, the surgical robot 501 may be configured to change the orientation of one or more interstitial catheters. According to control signals with real-time adjustments from a treatment controller 207 to the afterloader 111, the surgical robot 501 can be configured to control a time period that the radiation source is located at a targeted position. This time period may be adapted during radiotherapy according to the IVD data received by the treatment controller 207. Likewise, the targeted position may be adapted during radiotherapy according to the IVD data received by the treatment controller 207.

Figure 6:
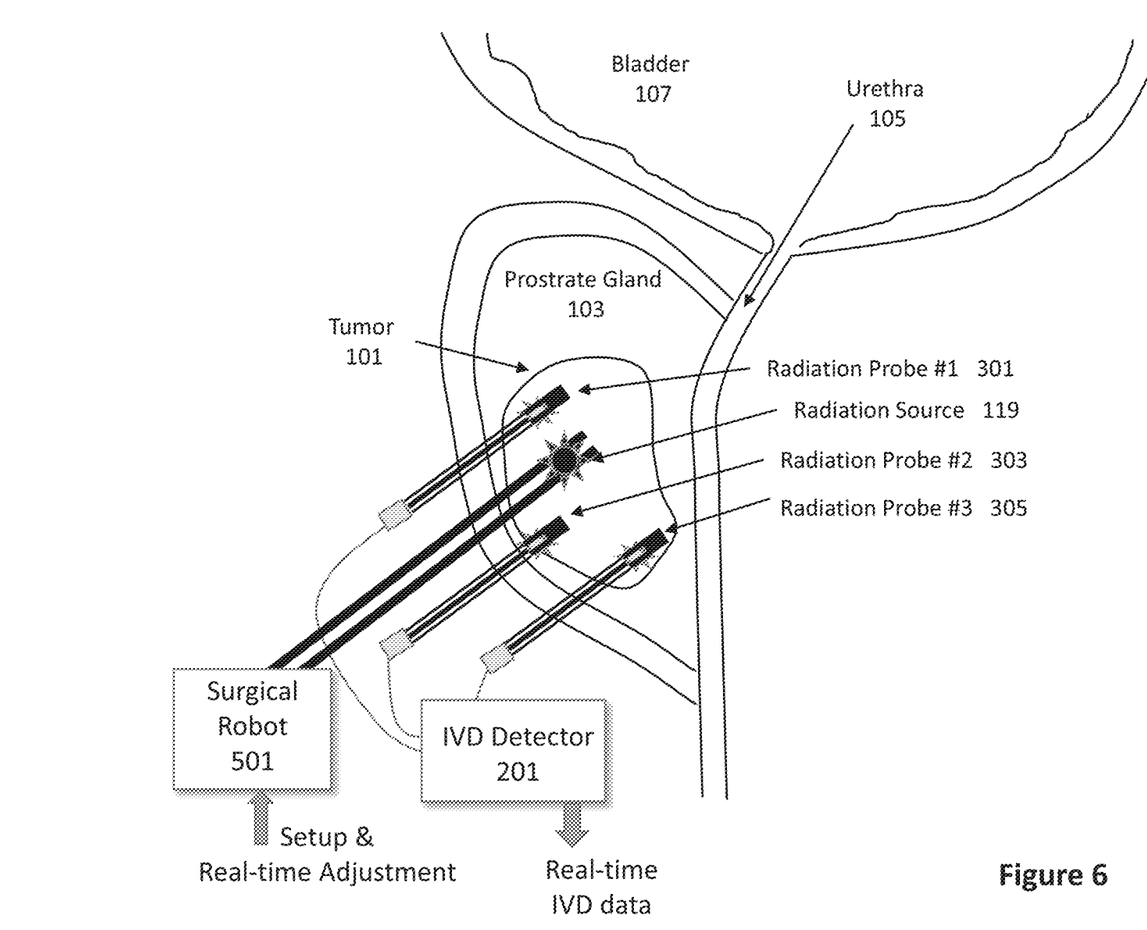
FIG. 6 illustrates the second placement option for an exemplary surgical robot in a system for adaptive radiotherapy in accordance with aspects of this disclosure.

FIG. 6 illustrates the second placement option for an exemplary surgical robot 501 in a system for adaptive radiotherapy in accordance with aspects of this disclosure. In FIG. 6, radiation probe #1 301, radiation probe #2 303, and radiation probe #3 305 are placed in the targeted tumor 101, while the surgical robot 501 administers the radiation treatment.

Figure 7:
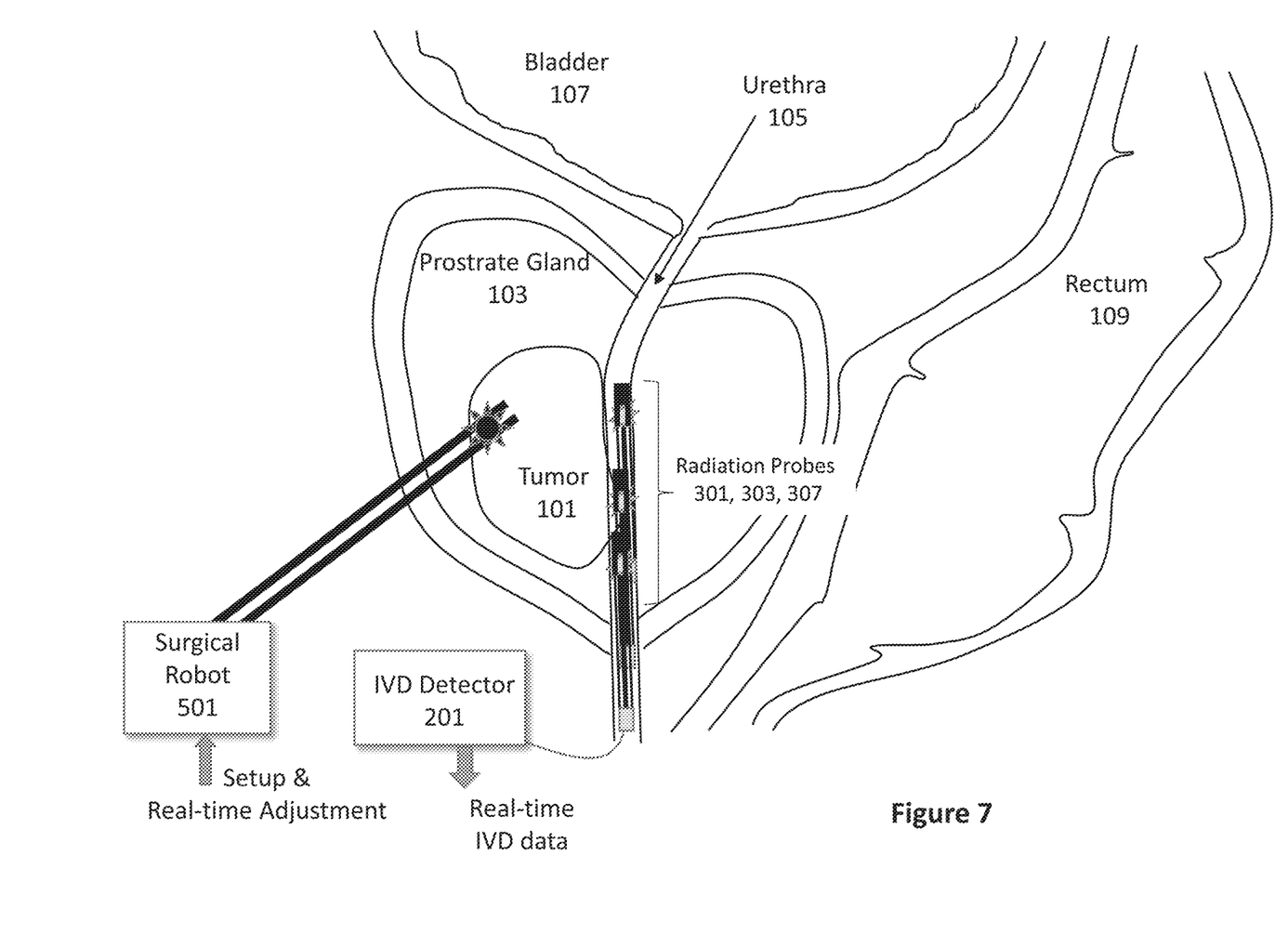
FIG. 7 illustrates the third placement option for an exemplary surgical robot in a system for adaptive radiotherapy in accordance with aspects of this disclosure.

FIG. 7 illustrates the third placement option for an exemplary surgical robot 501 in a system for adaptive radiotherapy in accordance with aspects of this disclosure. In FIG. 7, radiation probe #1 301, radiation probe #2 303, and radiation probe #3 305 are placed in the patient's urethra 105, while the surgical robot 501 administers the radiation treatment. The radiation probes 301, 303 and 305 may be located within or integrated into a urinary catheter.

Figure 8:
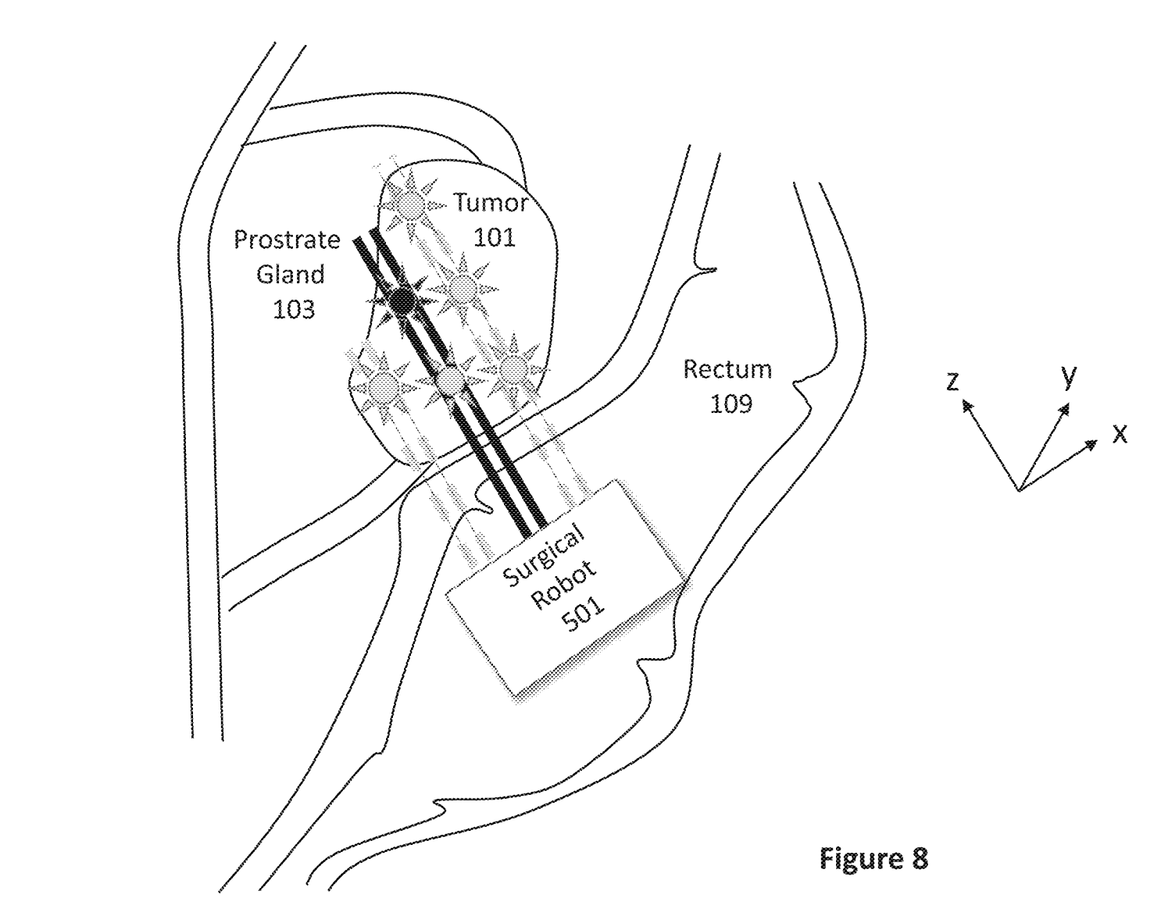
FIG. 8 illustrates the fourth placement option for an exemplary surgical robot in a system for adaptive radiotherapy in accordance with aspects of this disclosure.

FIG. 8 illustrates the fourth placement option for an exemplary surgical robot 501 in a system for adaptive radiotherapy in accordance with aspects of this disclosure. In FIG. 8, the surgical robot 501 administers the radiation treatment to the tumor 101 while being located in the patient's rectum 109.

Figure 9:
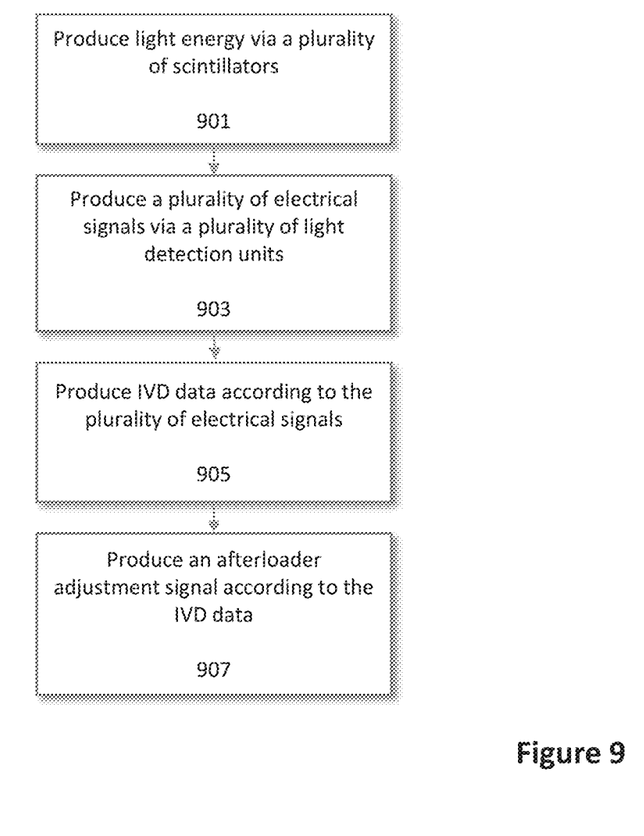
FIG. 9 illustrates an example method for adaptive radiotherapy in accordance with aspects of this disclosure.

FIG. 9 illustrates an example method for adaptive radiotherapy in accordance with aspects of this disclosure. At 901, light is produced via a plurality of scintillators. The level of the light produced by each scintillator is proportional to a level radiation and nature of a radiation source, incident to each scintillator. At 903, a plurality of electrical signals is produced via a plurality of light detection units. The level of the electrical signal produced by each light detection unit is proportional to the light from each corresponding scintillator. The current location and current velocity of the radiation source may be determined by triangulation according to the electrical signals from the plurality of light detection units.

At 905, IVD data is produced according to the plurality of electrical signals. The IVD data may be wirelessly transmitted from an IVD detector to the treatment controller. An error between a targeted location (i.e., the location determined prior to radiotherapy) of the radiation source and a current location of the radiation source may be computed from the IVD data. An error between a desired dosage of radiation and a current dosage of radiation may also be determined according to the electrical signals from the plurality of light detection units.

At 907, an afterloader adjustment signal is produced according to the IVD data. The afterloader adjustment signal may be used to control and adapt the time period that the radiation source is located at a targeted position. A surgical robot may be controlled according to the afterloader adjustment signal. The surgical robot may therefore control the placement of one or more interstitial catheters based on real-time feedback regarding the effectiveness and accuracy of the current radiotherapy, thereby reducing error and the need for retreatment.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise first "circuitry" when executing a first one or more lines of code and may comprise second "circuitry" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

What is claimed is:

1. A system for radiotherapy comprising:
a treatment controller operable to receive in-vivo dosimetry (IVD) data according to light received, from a plurality of scintillators in a presence of a radiation source, by a plurality of light detection units; and
a visual display configured to overlay a treatment plan on a real-time image of the plurality of scintillators.

2. The system of claim 1, wherein the system comprises an IVD detector that is configured to calculate a location of the radiation source according to electrical signals from the plurality of light detection units.

3. The system of claim 2, wherein the IVD detector is configured to wirelessly transmit the IVD data to the treatment controller.

4. The system of claim 1, wherein an IVD detector is configured to calculate a location of the radiation source by triangulation according to electrical signals from the plurality of light detection units.

5. The system of claim 1, wherein an IVD detector is configured to calculate a velocity of the radiation source according to electrical signals from the plurality of light detection units.

6. The system of claim 1, wherein the treatment controller is operable to calculate an error between a desired dosage of radiation and a current dosage of radiation, and wherein the desired dosage of radiation is determined prior to radiotherapy, and wherein the current dosage of radiation is determined according to the IVD data.

7. The system of claim 1, wherein the system comprises a surgical robot that is configured to control a placement of one or more interstitial catheters according to a treatment controller adjustment signal.

8. The system of claim 7, wherein:
the system comprises an afterloader, and
the afterloader is configured, according to the treatment controller adjustment signal, to control a time period that the radiation source is located at a targeted position.

9. The system of claim 8, wherein the time period is configured to be adapted during radiotherapy according to the IVD data received by the treatment controller.

10. The system of claim 8, wherein the targeted position is configured to be adapted during radiotherapy by the surgical robot and the afterloader according to the IVD data received by the treatment controller.

11. A method for radiotherapy comprising:
receiving light, via a plurality of light detection units, from a plurality of scintillators in a presence of a radiation source;
receiving in-vivo dosimetry (IVD) data, via a treatment controller, according to the light received from the plurality of scintillators; and
displaying a treatment plan overlaid on a real-time image of the plurality of scintillators.

12. The method of claim 11, wherein the method comprises:
calculating a location of the radiation source according to electrical signals from the plurality of light detection units.

13. The method of claim 11, wherein the method comprises:
calculating a location of the radiation source, by triangulation, according to electrical signals from the plurality of light detection units.

14. The method of claim 13, wherein the method comprises:
wirelessly transmitting the IVD data to the treatment controller.

15. The method of claim 11, wherein the method comprises:
calculating a velocity of the radiation source according to electrical signals from the plurality of light detection units.

16. The method of claim 11, wherein the method comprises:
determining a desired dosage of radiation prior to radiotherapy;
determining a current dosage of radiation according to the IVD data; and
calculating an error between the desired dosage of radiation and the current dosage of radiation.

17. The method of claim 11, wherein the method comprises:
controlling a placement of one or more interstitial catheters according to a treatment controller adjustment signal.

18. The method of claim 17, wherein the method comprises:
controlling a time period that the radiation source is located at a targeted position.

19. The method of claim 18, wherein the method comprises:
adapting the time period, during radiotherapy, according to the IVD data received by the treatment controller.

20. The method of claim 18, wherein the method comprises:
adapting the targeted position, via a surgical robot and an afterloader during radiotherapy, according to the IVD data received by the treatment controller.

* * * * *